(12) United States Patent
Fuchs et al.

(10) Patent No.: US 6,188,478 B1
(45) Date of Patent: Feb. 13, 2001

(54) METHOD AND APPARATUS FOR FILM-THICKNESS MEASUREMENTS

(75) Inventors: Martin Fuchs, Uxbridge; Michael A. Joffe, Wrentham; Matt Banet, Boston, all of MA (US)

(73) Assignee: Philips Electronics North America Corporation, New York, NY (US)

( * ) Notice: Under 35 U.S.C. 154(b), the term of this patent shall be extended for 0 days.

(21) Appl. No.: 09/176,174

(22) Filed: Oct. 21, 1998

(51) Int. Cl.[7] ............................. G01B 11/06; G01N 21/00
(52) U.S. Cl. ............................................. 356/381; 356/432
(58) Field of Search ................................ 356/432, 432 T, 356/381

(56) References Cited

U.S. PATENT DOCUMENTS

| 5,377,006 | * | 12/1994 | Nakata ............................... 356/349 |
| 5,479,259 | * | 12/1995 | Nakata et al. ........................ 356/432 |
| 5,734,470 | * | 3/1998 | Rogers et al. ....................... 356/432 |
| 5,812,261 | * | 9/1998 | Nelson et al. ....................... 356/318 |

FOREIGN PATENT DOCUMENTS

WO 98/03044    1/1998 (WO) ........................... H05B/37/00

* cited by examiner

*Primary Examiner*—Frank G. Font
*Assistant Examiner*—Zandra V. Smith
(74) *Attorney, Agent, or Firm*—Tony E. Piotrowski

(57) ABSTRACT

The invention describes a method for measuring a property of a sample by: 1) irradiating a portion of the sample with an excitation pattern characterized by at least one spatial phase and spatial period; 2) diffracting a portion of a probe beam off a surface of the sample; 3) detecting the diffracted portion of the probe beam with an optical detector to generate a light-induced signal; 4) adjusting the spatial phase of the excitation pattern; 5) repeating the irradiating, diffracting and detecting steps to generate an additional light-induced signal; and 6) processing the light-induced signals to determine a property of the sample.

33 Claims, 5 Drawing Sheets

METHOD AND APPARATUS FOR FILM-THICKNESS MEASUREMENTS

FIELD

This invention relates to a method and apparatus for measuring properties of a sample, e.g., the thickness of a thin film.

BACKGROUND

An all-optical measurement technique called Impulsive Stimulated Thermal Scattering (ISTS) measures a variety of different material properties, such as film thickness. In ISTS, two or more excitation laser beams from an excitation laser overlap in time and space on a surface of a sample to form a spatially varying optical interference pattern. The excitation laser beam consists of a series of short (e.g., a few hundred picoseconds) optical pulses having a wavelength within the absorption range of the sample. The excitation pattern features alternating "light" (i.e. constructive interference) and "dark" (i.e. destructive interference) elliptical regions with a spacing that depends on the wavelength of the laser beams and the angle between them. The light regions of the pattern heat the sample, causing it to thermally expand. This launches coherent, counter-propagating acoustic waves whose wavelength and direction match the pattern.

For opaque films (e.g., metal films), the acoustic waves generate a time-dependent "ripple" pattern on the film's surface that oscillates at one or more acoustic frequencies (typically a few hundred megahertz). The acoustic frequency depends on film properties such as thickness, density, and elastic moduli. A probe beam then diffracts off the ripple to form a series of signal beams, each representing at least one distinct diffraction order (e.g., the +1, −1, +2, or −2 orders). The signal beams oscillate in intensity at the acoustic frequency or a multiple thereof, or at sums or differences of acoustic frequencies if several are present. One or more of the signal beams is detected and monitored to measure the properties of the sample.

Use of ISTS to measure film thickness and a variety of other properties is described, for example, in pending and issued U.S. Pat. No. 5,633,711 (entitled MEASUREMENT OF MATERIAL PROPERTIES WITH OPTICALLY INDICED PHONONS); U.S. Pat. No. 5,546,811 (entitled OPTICAL MEASUREMENT OF STRESS IN THIN FILM SAMPLES); and U.S. Ser. No. 08/783,046 (entitled METHOD AND DEVICE FOR MEASURING FILM THICKNESS, filed Jul. 15, 1996), the contents of which are incorporated herein by reference.

ISTS-measured film thickness can be used as a quality-control parameter during and/or after the manufacturing of microelectronic devices. In these devices, thin films of metals and metal alloys are deposited on silicon wafers and used as electrical conductors, adhesion-promoting layers, and diffusion barriers. For example, metal films of copper, tungsten, and aluminum are used as electrical conductors and interconnects; titanium and tantalum as adhesion-promoting layers; and titanium:nitride and tantalum:nitride as diffusion barriers. Thickness variations in the metal films can modify their electrical and mechanical properties, thereby affecting the performance of the devices in which they are used. To effectively monitor metal films in a fabrication process, the ISTS film-thickness measurement must therefore be highly repeatable, precise, and accurate.

SUMMARY

To address these needs, the invention provides a method and apparatus for improving the repeatability, precision, and, in some cases, accuracy of film thickness measurements made using ISTS. Each improvement is attributed to "dithering" an optical or mechanical element in the system used for ISTS. In this case, "dither" is defined as any movement or modulation of a component that changes a spatial phase of the excitation pattern. In the preferred embodiment, the pattern consists of alternating light and dark regions as described above that are roughly parallel. Changing the spatial phase of the excitation pattern means that the positions of the light and dark regions of the excitation pattern are moved in concert relative to the surface of the sample. The change of spatial phase as a result of dither is preferably in a direction perpendicular to the orientation of the long axis of the elliptical light and dark regions. The terms phase and spatial phase will be used interchangeably herein with respect to the excitation pattern.

In general, in one aspect, the invention provides a method for measuring a sample that includes the steps of: 1) irradiating a portion of the sample with an excitation pattern characterized by at least one spatial phase and spatial period; 2) diffracting a portion of a probe beam off a surface of the sample; 3) detecting the diffracted portion of the probe beam with an optical detector to generate a light-induced signal; 4) adjusting the phase of the excitation pattern; 5) repeating the irradiating, diffracting and detecting steps to generate an additional light-induced signal; and 6) processing the light-induced signals to determine a property of the sample.

In another aspect, the invention provides an apparatus for measuring a sample that includes: 1) a first light source that generates an optical excitation pulse; 2) an optical system aligned to receive the optical excitation pulse, separate it into at least two optical pulses, and focus at least one pulse onto a surface of the sample to form an excitation pattern characterized by at least one spatial phase and spatial period; 3) a phase-adjusting component that adjusts the spatial phase of excitation pattern; 4) a second light source that generates a probe beam that diffracts off the sample; 5) an optical detector that detects the diffracted portion of the probe beam to generate a light-induced signal; and 6) a processor configured to process the light-induced signal from the optical detector to determine a property of the sample.

Further advantageous embodiments of the invention are recited in the dependent claims.

The invention has many advantages. In general, using dithering to vary the phase of the excitation pattern during a measurement improves the precision of ISTS-based thickness measurements: even very rough films, or films with regions containing areas that scatter radiation, can be accurately measured. In this application, ISTS detects minor variations in the thickness of thin films that can affect their functions in microelectronic devices.

The improvement in precision is particularly evident in multi-point measurements. These measurements involve making thickness measurements from multiple points within a given area. Examples of multi-point measurements include: 1) "line scans" that measure more than one point along a line on a film's surface, e.g., along a film's diameter or edge; and 2) "contour maps" based on a two-dimensional array of points measured in an area (e.g., a circle, square, or rectangle) on the film. During these multi-point measurements, dithering a component of the optical system decreases the standard deviation of the thickness measured from each point, thereby increasing the overall precision of the measurement.

In a more general sense, the invention improves an all-optical, non-contact measurement technique that effectively measures the thickness of thin films in single and multi-layer structures, such as ISTS. The thickness values can then be used to control a fabrication process (e.g., fabrication of a microelectronic device). The apparatus features all the advantages of optical metrology: each measurement is non-contact, rapid (typically less than 1 or 2 seconds per point), remote (the optical system can be as far as 10 cm or more from the sample), and can be made over a small region (as small as about 20 microns). Other properties besides film thickness may also be measured more precisely through the use of dithering.

DETAILED DESCRIPTION

Figure 1A:
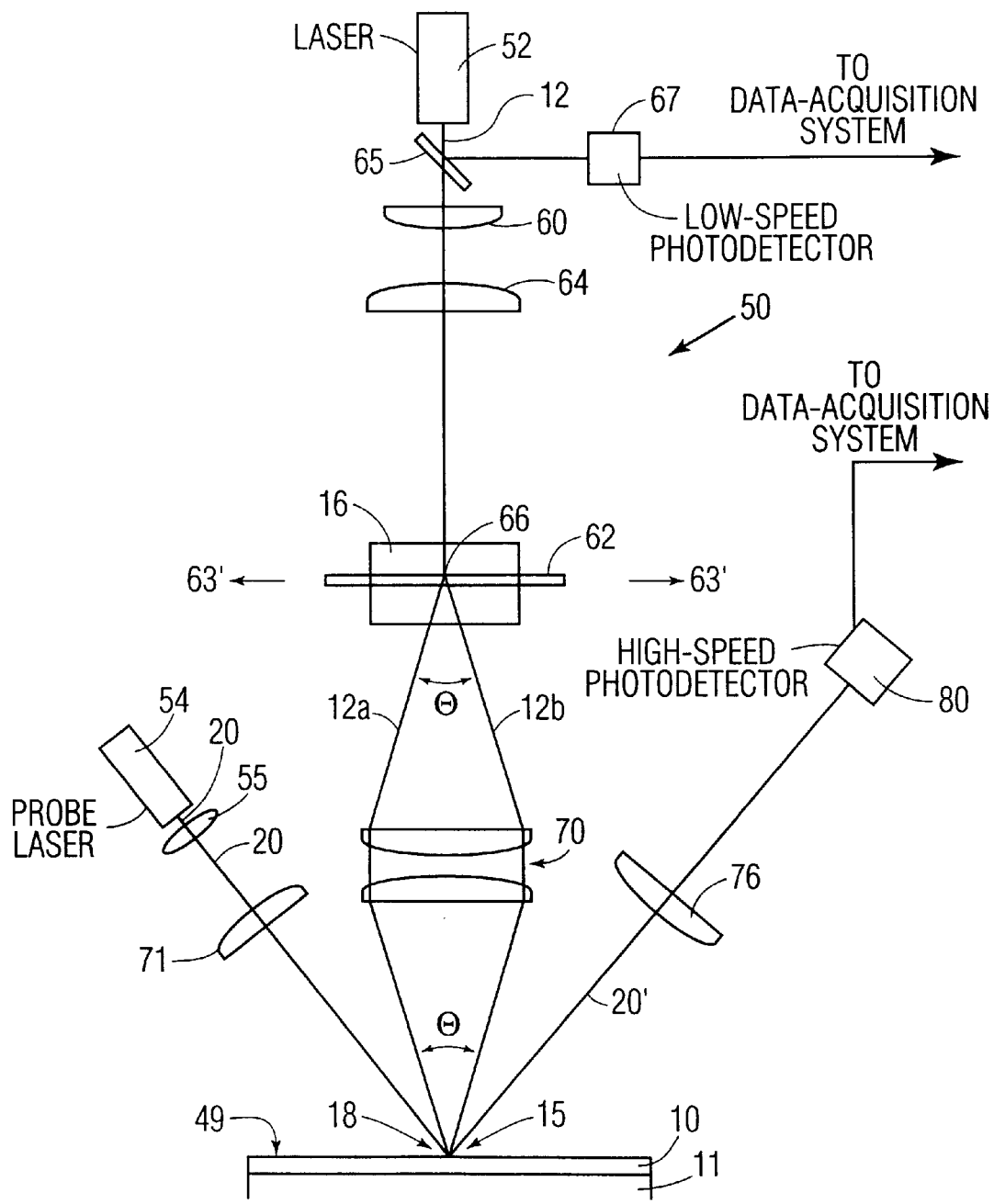
FIG. 1A shows an optical system for performing the ISTS measurement that includes a dithered phase mask according to the invention.
Figure 1B:
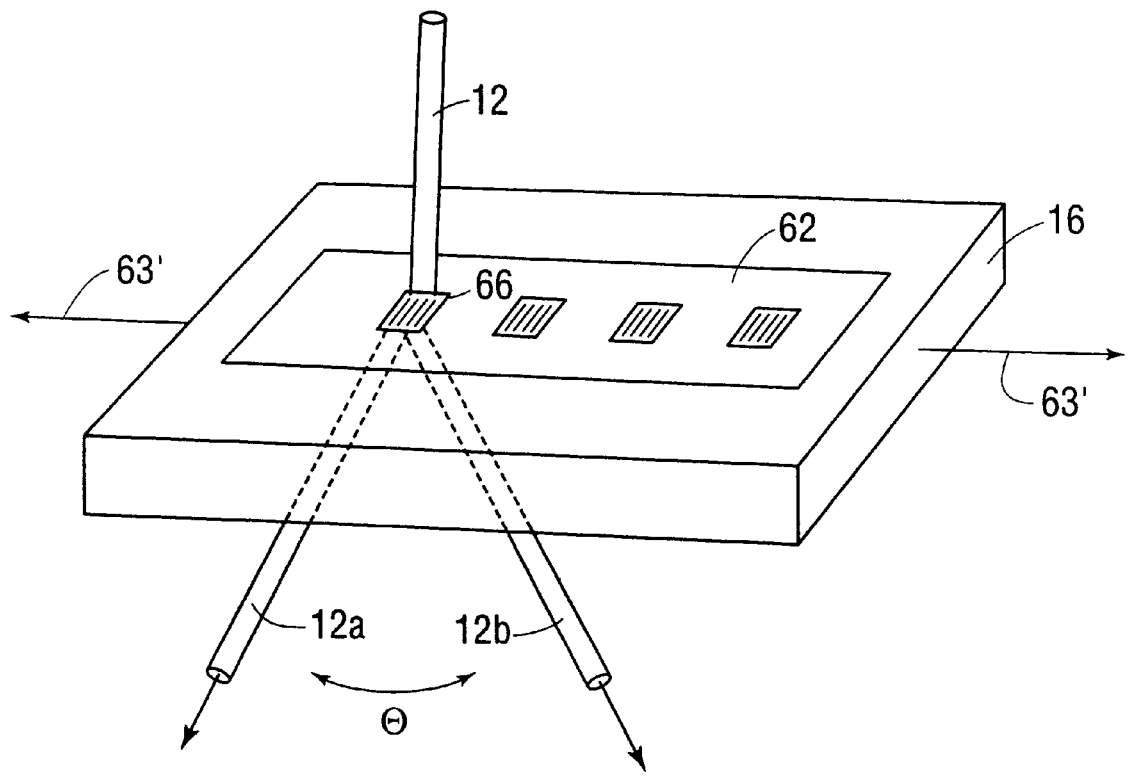
FIG. 1B shows a close-up view of the dithered phase mask of FIG. 1A.
Figure 1C:
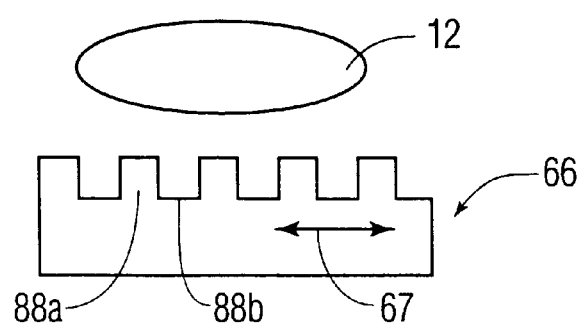
FIG. 1C shows a schematic side view of the pattern on the phase mask of FIG. 1A.

Referring to FIGS. 1A–C, an optical system 50 uses ISTS to measures the thickness of a thin film 10 disposed on a substrate 11. Similar optical systems are described in U.S. Pat. No. 5,633,711 (entitled MEASUREMENT OF MATERIAL PROPERTIES WITH OPTICALLY INDICED PHONONS); U.S. Pat. No. 5,546,811 (entitled OPTICAL MEASUREMENT OF STRESS IN THIN FILM SAMPLES); and U.S. Ser. No. 08/783,046 (entitled METHOD AND DEVICE FOR MEASURING FILM THICKNESS, filed Jul. 15, 1996), the contents of which have been previously incorporated herein by reference. The system 50 features a microchip laser 52 that emits an excitation pulse 12 that passes through a beam-splitter 65. The beam-splitter 65 reflects a portion of the pulse into a low-speed photo-detector 67 to generate an electrical pulse that triggers a data-acquisition system (not shown in the figure). The remainder of the excitation pulse 12 travels through the beam splitter 65 and impinges a spherical collimating lens 60 and a cylindrical focussing lens 64 that focus the pulse onto a phase mask 62.

Referring to FIGS. 1B–1C, the phase mask 62 attaches to a motor-driven stage 16 that, during a measurement, "dithers" back and forth to translate the mask 62 horizontally relative to the propagation of the excitation pulse 12. As indicated by the arrow 63', dithering is typically performed in a time-dependent, periodic manner (e.g., a sinusoidal manner). During dithering the excitation pulse 12 irradiates a pattern 66 on the phase mask 62 that consists of glass etched to include regions 88a, 88b having different thicknesses. As indicated by the arrow 67 in FIG. 1C, the regions 88a, 88b are spaced by a distance (typically between 1 and 50 microns) that is smaller than a spot size of the laser pulse. The spot size is typically elliptical with dimensions of approximately 20×200 microns; the long axis of the ellipse extends orthogonal to the extension of the regions 88a, 88b. During typical applications, the phase mask translates back and forth over a range of about 0.01 mm–2.0 mm with a velocity of about 50 microns/second.

The range of the dither is typically similar to the spacing of the pattern on the phase mask, described above as being between 1 and 50 microns. In general, it is preferred that dithering the phase mask vary the spatial phase of the excitation pattern in an incremental fashion ranging from 0° to 180°, or some multiple thereof. Since the excitation pattern is preferably a sequence of parallel light and dark regions, this means that the light regions will move to where the dark regions were and the dark regions will move to where the light regions were, and back again, during dither.

In this configuration, the pattern 66 diffracts the pulse 12 into two excitation pulses 12a, 12b that diverge from the mask 62 at an angle θ. During operation, dithering of the phase mask causes the position of the regions 88a, 88b to vary relative to the elliptical laser spot in a time-dependent manner. This process modulates the optical phase of each excitation pulse 12a, 12b and, consequently, the phase of the light and dark regions of the excitation pattern when the excitation pulses are overlapped on the sample surface. During a typical measurement, Dithering occurs at a frequency (typically 100–1000 Hz) that is higher than the data-acquisition frequency (typically 10–500 Hz) of the ISTS measurement, so that several ISTS measurements are performed within each dither cycle.

Referring again to FIG. 1A, the excitation pulses 12a, 12b diverge from the phase mask 62 and irradiate an achromatic lens pair 70 having a focal length f. The lens pair 70 focuses the pulses 12a, 12b onto the film 10 at the same angle θ that the pulses diverge from the phase mask. The lens pair 70 overlaps the pulses on a surface 49 of the film 10 so that they optically interfere to form a spatially periodic excitation pattern 15. The pattern 15 features between about 50 alternating light and dark regions. The lens pair 70 is separated from the phase mask by a distance of 2 f so that the excitation pattern 15 has a spatial frequency that matches the spatial frequency of the pattern 66 on the phase mask (i.e., the achromatic lens pair approximately performs 1:1 imaging). Dithering the phase mask as described above adjusts the spatial phase of the excitation pattern relative to the sample in a time-dependent manner, but does not change its spatial frequency.

During an ISTS measurement, the film absorbs the light regions in the pattern 15 and, in response, thermally expands to launch counter-propagating acoustic waves. The acoustic waves form a "transient grating" that modifies the film's surface (e.g., by generating a time-dependent surface ripple or refractive index change) at the acoustic frequency. Once initiated, the acoustic waves are measured with a probe beam 20 emitted from a probe laser 54. The probe beam 20 passes through a collimating lens 55 and a spherical lens 71 that focus the beam so that it irradiates the film's surface at or near the pattern. A portion of the probe beam diffracts off the surface waves to form a diffracted signal beam 20' that passes through a lens 76 and into a high-speed photodetector 80. The photodetector 80 detects the diffracted beam 20' to generate a light-induced electrical signal that is processed by the data-acquisition system to generate a data sweep that is modulated at the acoustic frequency. In other words, the term "data sweep" will be used herein to refer to a single measurement.

Figure 2A:
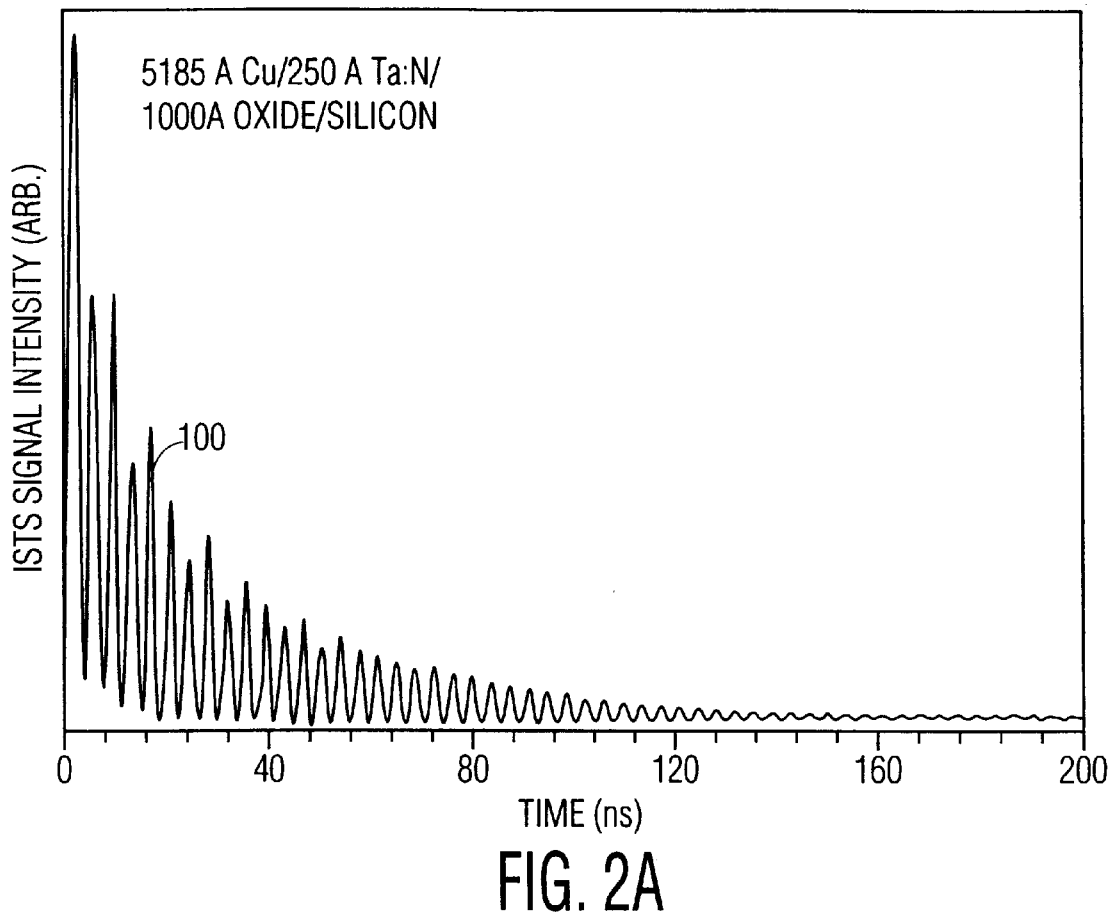
FIG. 2A shows a plot of signal intensity versus time for a signal waveform measured from a copper/tantalum:nitride/oxide structure deposited on a silicon wafer.
Figure 2B:
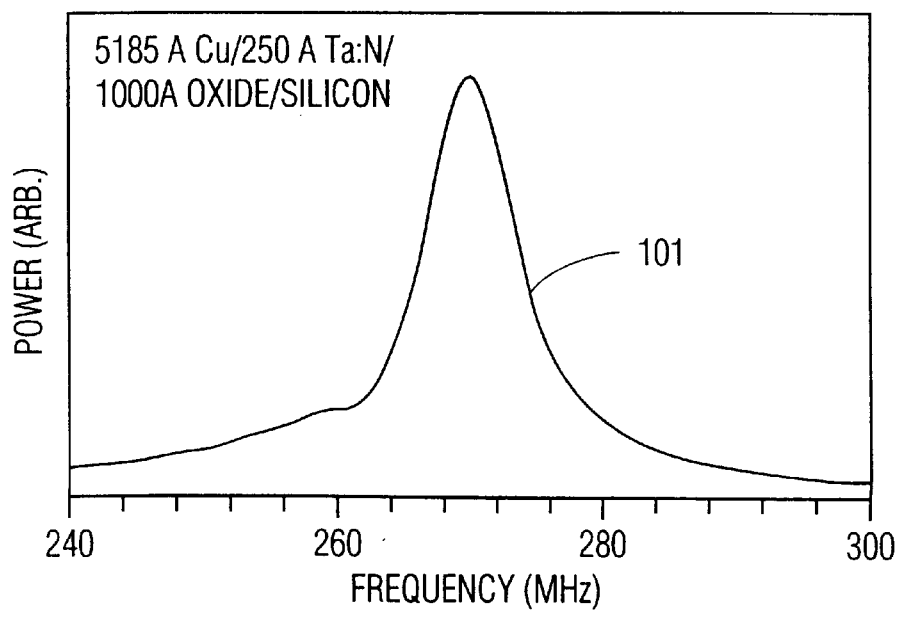
FIG. 2B shows the Fourier Transform of FIG. 2A.

During a typical measurement, a computer (not shown in the figure) averages multiple data sweeps (typically 50–500 sweeps) from a single spot to generate a signal waveform 100, such as that shown in FIG. 2A. Thus, in this application, the phase mask is dithered within the ISTS measurement. Averaging data sweeps in this way results in data having high signal-to-noise ratios (typically 1 part in 100,000). The signal waveform 100 shown in FIG. 2A was measured from a nominal 5185-angstrom copper/250-angstrom/1000-angstrom oxide structure deposited on a silicon wafer, and shows an ISTS signal intensity (in units of millivolts) plotted as a function of time (in units of nanoseconds). The Fourier transform 101 of the signal waveform 100 is indicated by the graph in FIG. 2B. These data indicate that the frequency of the signal waveform, and thus the frequency of the acoustic mode, in this case is about 270 MHz. To determine film thickness, this acoustic frequency is analyzed by a computer along with the inverse of the spacing between the light and dark regions of the excitation pattern (i.e., the wavevector) and the film's density and sound velocities as described in the above-mentioned references. The analysis process is described, e.g., in U.S. Pat. No. 5,633,711, the contents of which are incorporated herein by reference. Measurements can be made at single or multiple points along the sample surface.

Figure 3A:
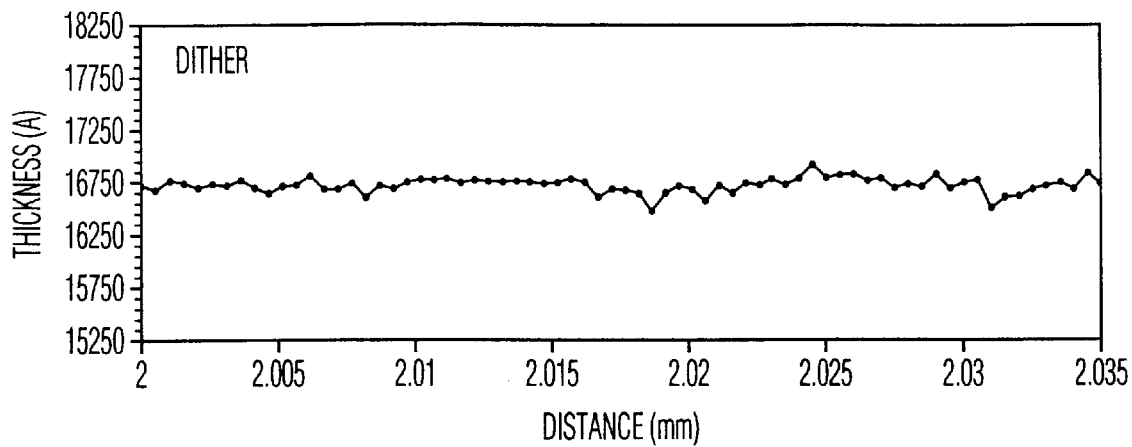
FIGS. 3A and 3B show plots of film thickness as a function of position generated from a linear multi-point measurements made, respectively, with and without dithering the phase mask of FIG. 1A.
Figure 3B:
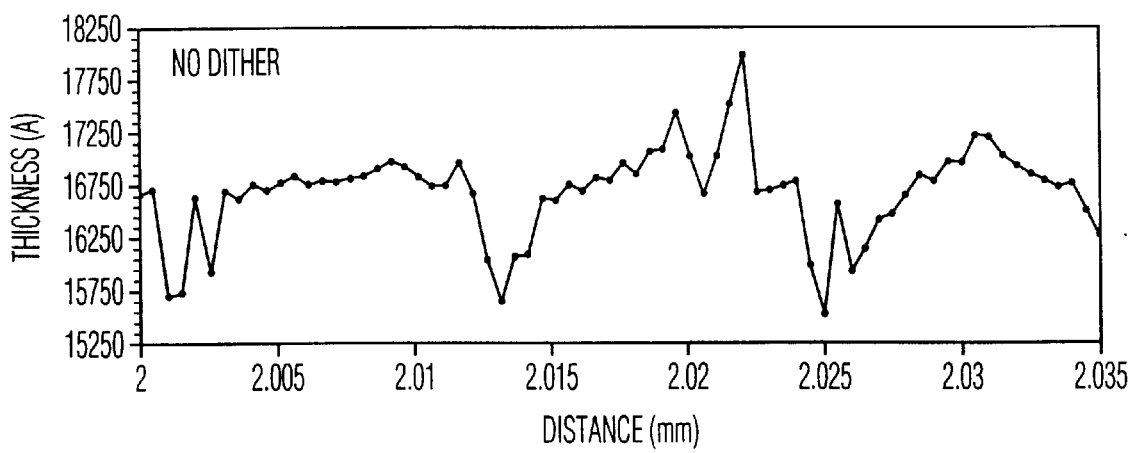

FIG. 3A and 3B show how dithering the phase mask improves the position-dependent thickness measurement using the above-described method. The y-axis for both figures has units of angstroms and the x-axis has units of mm. Data for the figures were taken using the sample described in FIG. 2 over a linear distance of 0.035 mm with dither (FIG. 3A) and without dither (FIG. 3B). To make the position-dependent thickness measurements, an ISTS measurement was taken every 0.5 microns. As is clear from the data, the measurement of film thickness using a dithered phase mask is more uniform (having a total range of about 75 angstroms) than a similar measurement made without dithering (having a total range of greater than 200 angstroms). Those of ordinary skill will immediately appreciate that the thickness excursions in FIG. 3b are not an accurate representation of the thickness of the copper film, while those shown in FIG. 3a are more typical.

Other Embodiments

Other embodiments are within the scope of the invention described above. In other words, other components of the optical system can be moved or altered in order to achieve the desired variation of the spatial phase of the excitation pattern. In each case, the preference is to dither the component so as to cause the spatial phase of the excitation pattern to vary between 0° and 180°.

Figure 4A:
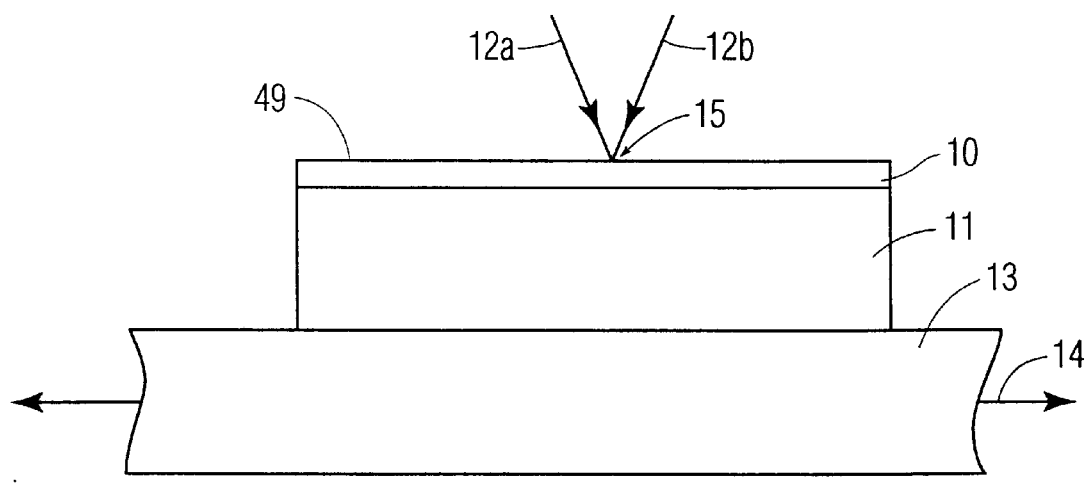
FIG. 4A shows a schematic side view of a dithered sample mount according to the invention.

In particular, referring to FIG. 4A, the phase of the excitation pattern can be adjusted in a time-dependent manner by translating a sample mount 13 that dithers horizontally back and forth (as indicated by the arrow 14). This method is analogous to dithering the phase mask, as it adjusts the spatial phase of the excitation pattern 15 relative to the sample's surface 49. In this case, the sample mount 13 translates over a distance and with a velocity similar to the values described for the dithered phase mask of FIGS. 1A and 1B.

Figure 4B:
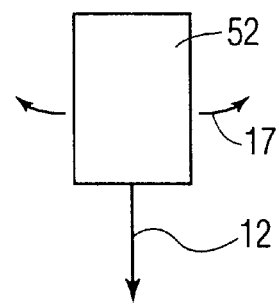
FIG. 4B shows a schematic side view of a dithered excitation laser according to the invention.

Referring to FIG. 4B, in another embodiment the excitation laser 52, a mirror (not shown), a lens (not shown), or a combination of these or other components in the optical system are dithered (as indicated by the arrow 17) to obtain the same result of dithering the phase mask as described above. Again, the range and velocity of the dithering is similar to that described with reference to FIGS. 1A and 1B.

In general, dithering is accomplished by moving any element of the system (e.g., the phase mask) with a motor-driven stage or equivalent that receives any type of electrical signal. The signal can be a sinusoidal, saw-tooth, square, random, or any other type of waveform between 0.1 and 1000 Hz. The motor-driven stage can be replaced with any movable component, such as a piezoelectric device.

Figure 4C:
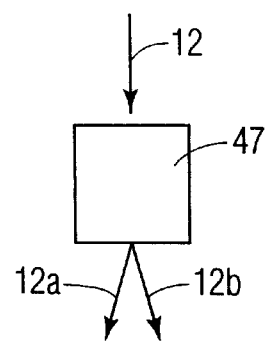
FIG. 4C shows a schematic side view of an acousto-optic modulator that dithers the excitation beam according to the invention.

As shown in FIG. 4C, dithering can alternatively be accomplished by placing an electro-optic (e.g., Pockels cell) or acousto-optic (e.g., Bragg cell) modulator 47 in the path of one of the excitation pulses shown in FIG. 4B. In this case, as is known in the art, the modulator varies the phase of the incident pulse 12 and simultaneously generates two excitation pulses 12a, 12b. When overlapped on the sample, these pulses form an excitation pattern that varies as a function of time.

In other embodiments, optical systems other than that shown in FIG. 1 that use a phase mask to generate an excitation field to excite acoustic waves and a reflection-mode geometry to measure the waves can be used. Such systems, for example, are described in U.S. Ser. No. 08/885,555 (entitled IMPROVED TRANSIENT-GRATING METHOD AND APPARATUS FOR MEASURING MATERIAL PROPERTIES), the contents of which are incorporated herein by reference.

Likewise, the phase mask can be replaced with a similar diffractive optical element, such as an amplitude mask, a diffraction grating, an electro-optic modulator, or some combination or equivalent thereof to generate the beams that form the excitation pattern. The diffractive element can include patterns that simultaneously generate more than one spatial frequency, an excitation pattern that is non-periodic, or an excitation pattern that contains light regions that are shapes other than a series of parallel lines. For example, the diffractive element may generate an excitation pattern consisting of a series of concentric circles, ellipses, or other shapes. Other acceptable patterns for diffractive masks are described in U.S. Pat. No. 5,734,470, entitled DEVICE AND METHOD FOR TIME-RESOLVED OPTICAL MEASUREMENTS, the contents of which have been previously incorporated herein by reference. In such cases, the dither of components may result in a change in the excitation pattern which is somewhat different from that described for the parallel light and dark regions. Nevertheless, a movement of such excitation patterns at a frequency somewhat greater than the data acquisition frequency can be achieved with beneficial effects.

Likewise, any suitable laser can be used to generate excitation and probe radiation. Typically the excitation and probe lasers are, respectively, a diode-pumped Nd:YAG/Cr$^{+4}$:YAG microchip laser and a diode laser, although other lasers can be used. For example, the excitation laser can be a titanium:sapphire, chromium:LISAF, ring, or fiber laser.

In still other embodiments the signal waveform can be analyzed to determine properties of the sample other than thickness. For example, the acoustic frequency can be used to determine adhesion, density, stiffness, elasticity, surface roughness, and other mechanical or physical properties of a thin film. In addition, delamination, portions of the signal waveform other than frequency can be analyzed to determine other properties about the sample. For example, the shape of the waveform can be analyzed to determine the degree of adhesion, surface roughness, or composition of one or more of the films in the structure.

Other properties that can be measured from the waveform include properties of ion-implanted silicon wafers, such as the concentration and energy of the implanted ions. Measurement of these properties are described, for example, in U.S. Ser. No. 08/783,046 (entitled METHOD AND APPARATUS FOR MEASURING IONS IMPLANTED IN SEMICONDUCTOR MATERIALS) and U.S. Ser. No. 08/885,555 (entitled IMPROVED METHOD AND APPARATUS FOR MEASURING IONS IMPLANTED IN SEMICONDUCTOR MATERIALS), the contents of which are incorporated herein by reference.

The method and apparatus of the invention can be used to measure a variety of structures. For example, the method is particularly effective in determining the thickness of metal films used in the microelectronic industry. Such metal films include but are not limited to aluminum, copper, tungsten, titanium, tantalum, titanium:nitride, tantalum:nitride, gold, platinum, niobium, and alloys thereof. These metals may be included in single-layer and multi-layer structures. Other materials that can be measured include semiconductors (e.g., silicon, GaAs, and derivatives thereof) polymers, diamond-like coatings, and buried transparent films.

Still other embodiments are within the scope of the following claims.

What is claimed is:

1. A method for measuring a sample, comprising the steps of:
    (a) irradiating a portion of the sample with an excitation pattern characterized by at least one spatial phase and spatial period;
    (b) diffracting a portion of a probe beam off a surface of the sample;
    (c) detecting the diffracted portion of the probe beam with an optical detector to generate a light-induced signal;
    (d) dithering the spatial phase of the excitation pattern;
    (e) repeating the irradiating, diffracting and detecting steps to generate an additional light-induced signal; and
    (f) processing the light-induced signals to determine a property of the sample.

2. The method of claim 1, wherein the diffractive pattern is formed by overlapping at least two optical pulses derived from an initial optical pulse.

3. The method of claim 2, wherein the initial optical pulse is passed through a diffractive element to form at least two optical pulses.

4. The method of claim 3, wherein the dithering step comprises moving the diffractive element.

5. The method of claim 4, wherein the moving step further comprises translating the diffractive element in a direction orthogonal to a direction of propagation of the initial optical pulse.

6. The method of claim 5, wherein the moving step further comprises moving the diffractive element with a movable component driven by an electrical signal.

7. The method of claim 6, wherein the movable component comprises a piezoelectric device, a motor, a mechanical stage, or a combination thereof.

8. The method of claim 6, wherein the electrical signal is a square, saw-tooth, triangular, random, or sinusoidal waveform.

9. The method of claim 4, wherein the moving step further includes moving the diffractive element in a continuous motion.

10. The method of claim 4, wherein the moving step further includes moving the diffractive element in an incremental motion.

11. The method of claim 10, wherein the moving step comprises moving the diffractive element in incremental steps that are smaller than the spatial period of the excitation pattern.

12. The method of claim 11, wherein the diffractive element is translated by multiple incremental steps over a total distance such that the spatial phase of the excitation pattern varies by an incremental value ranging from 0° to 180°.

13. The method of claim 12, wherein the spatial period is between 0.1 and 500 microns.

14. The method of claim 1, wherein each light-induced signal is a time-dependent signal waveform.

15. The method of claim 14, wherein the processing step further comprises averaging multiple light-induced signals.

16. The method of claim 15, wherein the processing step further comprises determining a Fourier transform of each light-induced signal or the average of the multiple light-induced signals.

17. The method of claim 1, wherein the method further includes an analysis step to determine a property of the sample.

18. The method of claim 17, wherein the analysis step further includes analyzing the light-induced signals with a computer or microprocessor.

19. The method of claim 18, wherein the sample is a film or a structure that includes a film, and the property is a thickness of the film.

20. The method of claim 19, wherein the film is included in a multi-film sample.

21. The method of claim 1, wherein the dithering step comprises moving a component of the optical system.

22. The method of claim 21, wherein the component of the optical system is a mirror, lens, or prim and the moving step further includes moving the mirror, the lens, the prism, or a combination thereof.

23. The method of claim 21, wherein a component of the optical system is a laser, and the moving step includes moving the laser.

24. The method of claim 1, wherein the phase dithering step further comprises moving the mount that supports the sample.

25. The method of claim 1, wherein the dithering step further comprises adjusting a phase of the excitation pattern with an electro-optic modulator, acousto-optic modulator, a moving glass slide, or a combination thereof.

26. An apparatus for measuring a sample, comprising:
    a) a first light source that generates an optical excitation pulse;
    b) an optical system aligned to receive the optical excitation pulse, separate it into at least two optical pulses, and focus at least one pulse onto a surface of the sample to form an excitation pattern characterized by at least one spatial phase and at least one spatial period;
    c) a phase-dithering component that dithers the spatial phase of excitation pattern while the sample is being measured;
    d) a second light source that generates a probe beam that diffracts off the sample;
    e) an optical detector that detects the diffracted portion of the probe beam to generate a light-induced signal; and
    f) a processor configured to process the light-induced signal from the optical detector to determine a property of the sample.

27. The apparatus of claim 26, wherein the optical system comprises a diffracting element.

28. The apparatus of claim 27, wherein the diffracting element is a phase mask, amplitude mask, diffraction grating, electro-optic modulator, or accousto-optic modulator.

29. The apparatus of claim 26, wherein the phase-dithering component comprises a moveable component.

30. The apparatus of claim 29, wherein the movable component comprises a motor or a piezoelectric device.

31. The apparatus of claim 26, wherein the first and second light sources are lasers.

32. The apparatus of claim 26, wherein the optical system includes a mechanical stage that supports the sample.

33. The apparatus of claim 26, wherein the processor is a computer or a microprocessor.

* * * * *